(12) United States Patent
Balthasar et al.

(10) Patent No.: US 9,594,040 B2
(45) Date of Patent: Mar. 14, 2017

(54) METHOD AND APPARATUS FOR ANALYZING METAL OBJECTS CONSIDERING CHANGING BELT PROPERTIES

(71) Applicant: TOMRA SORTING AS, Asker (NO)

(72) Inventors: Dirk Balthasar, Boppard (DE);
Thomas Erdmann, Koblenz (DE);
Volker Rehrmann, Koblenz (DE);
Stefan Jürgensen, Pinneberg (DE);
Slah Gharbi, Pinneberg (DE)

(73) Assignee: TOMRA SORTING AS, Asker (NO)

( * ) Notice: Subject to any disclaimer, the term of this patent is extended or adjusted under 35 U.S.C. 154(b) by 0 days.

(21) Appl. No.: 14/421,925

(22) PCT Filed: Aug. 16, 2013

(86) PCT No.: PCT/NO2013/050131
§ 371 (c)(1),
(2) Date: Feb. 16, 2015

(87) PCT Pub. No.: WO2014/027896
PCT Pub. Date: Feb. 20, 2014

(65) Prior Publication Data
US 2015/0212023 A1 Jul. 30, 2015

(30) Foreign Application Priority Data
Aug. 16, 2012 (EP) .................... 12180634

(51) Int. Cl.
*B07C 5/344* (2006.01)
*G01N 27/00* (2006.01)
*B07C 5/36* (2006.01)

(52) U.S. Cl.
CPC ............. *G01N 27/00* (2013.01); *B07C 5/344* (2013.01); *B07C 5/361* (2013.01)

(58) Field of Classification Search
CPC .. B07C 5/344; B07C 5/361366; G01N 27/023
See application file for complete search history.

(56) References Cited

U.S. PATENT DOCUMENTS 4,439,731 A * 3/1984 Harrison ................ G01R 33/12
324/239
5,257,206 A * 10/1993 Hanson ................ F25J 3/04303
700/273
(Continued)

FOREIGN PATENT DOCUMENTS

| CN | 2597109 Y | 1/2004 |
| CN | 101522322 A | 9/2009 |

(Continued)

OTHER PUBLICATIONS

International Search Report (PCT/ISA/210) mailed on Dec. 6, 2013, by the Norway Patent Office as the International Searching Authority for International Application No. PCT/NO2013/050131.
(Continued)

*Primary Examiner* — Joseph C Rodriguez
(74) *Attorney, Agent, or Firm* — Buchanan Ingersoll & Rooney P.C.

(57) ABSTRACT

A method for analyzing objects depending on their electromagnetic properties. The method including the steps of conveying the objects to be analyzed on a conveyer belt; scanning the electromagnetic properties of the objects and the conveyer belt by an electromagnetic sensor, wherein the electromagnetic properties of the conveyer belt are dependent on metallic contaminants which are stuck in the conveyer belt; generating belt properties data representing the electromagnetic properties of the conveyer belt, and analyzing the objects according to the scanned electromagnetic properties and the belt properties data. This has the benefits that the electromagnetic properties of the conveyer belt are considered when distinguishing between metallic and non-
(Continued)

metallic objects which have to be sorted. This way, the objects which got stuck in the conveyer belt over time, may influence a sorting less, which may improve sorting results. Further, an apparatus for executing such a method.

27 Claims, 6 Drawing Sheets

(56) References Cited

U.S. PATENT DOCUMENTS

| | | | | |
|---|---|---|---|---|
| 6,847,447 B2* | 1/2005 | Ozanich | ................. | G01J 3/02 209/588 |
| 7,367,457 B2* | 5/2008 | Warlitz | ................. | B03C 1/14 209/225 |
| 7,726,493 B2* | 6/2010 | Van Der Weijden | ..... | B03B 9/04 209/12.1 |
| 7,786,401 B2* | 8/2010 | Valerio | ................. | B07C 5/368 209/143 |
| 8,158,902 B2* | 4/2012 | Valerio | ................. | B07C 5/344 209/556 |
| 8,875,901 B2* | 11/2014 | Wellwood | ................. | B07C 5/34 209/552 |
| 9,221,061 B2* | 12/2015 | Rem | ................. | B03C 1/247 |
| 2007/0262000 A1 | 11/2007 | Valerio | | |
| 2010/0164512 A1 | 7/2010 | Kiss et al. | | |
| 2010/0282646 A1* | 11/2010 | Looy | ................. | B07C 5/344 209/12.1 |
| 2015/0347815 A1* | 12/2015 | Dante | ................. | A24B 3/16 382/191 |
| 2016/0299091 A1* | 10/2016 | Bamber | ................. | B07C 5/344 |

FOREIGN PATENT DOCUMENTS

| | | |
|---|---|---|
| EP | 1 347 311 A2 | 9/2003 |
| EP | 1 416 265 A1 | 5/2004 |
| WO | 2008/101270 A1 | 8/2008 |
| WO | WO 2011/082728 A1 | 7/2011 |

OTHER PUBLICATIONS

Written Opinion (PCT/ISA/237) mailed on Dec. 6, 2013, by the Norway Patent Office as the International Searching Authority for International Application No. PCT/NO2013/050131.

European Search Report (EPO Form 1507N) mailed Jan. 23, 2013 for Application No. 12180634.3-2307.

Search Report dated Jan. 25, 2016, issued by the Chinese Patent Office in the corresponding Chinese Application No. 2013800425838. (3 pages).

* cited by examiner

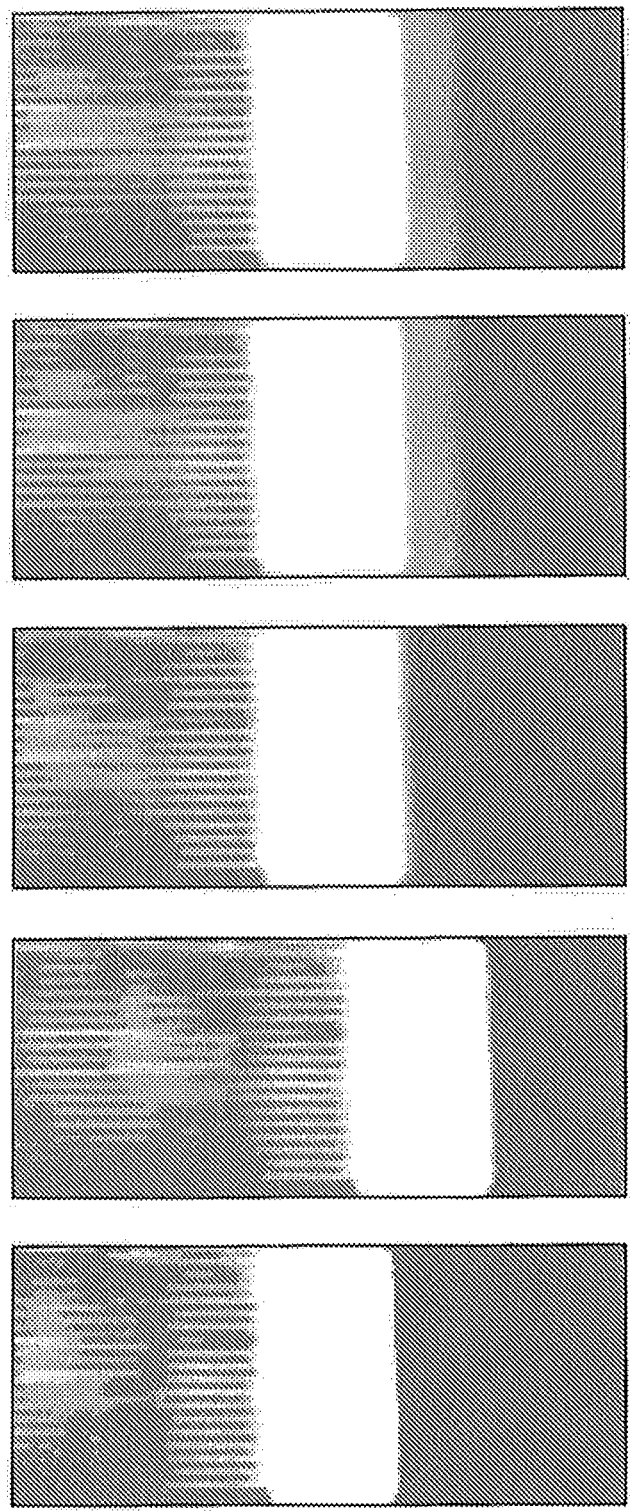

METHOD AND APPARATUS FOR ANALYZING METAL OBJECTS CONSIDERING CHANGING BELT PROPERTIES

The invention relates to a method and an apparatus for analyzing objects depending on their electromagnetic properties, such as for analyzing and sorting them into non-metallic and metallic objects, and/or such as for analyzing and sorting the metallic objects according to their kind of metal.

BACKGROUND OF THE INVENTION

In metal sorting devices, objects to be sorted are conveyed on a conveyer belt and sorted according to their electromagnetic properties. In order to determine their electromagnetic properties, the objects which are conveyed on the conveyer belt are scanned by an electromagnetic scanner or sensor. The electromagnetic sensor identifies metallic objects and a processor activates one or more air nozzles located downstream in a conveying direction to blow the metallic objects into a container which collects them. In case of the non-metallic objects, the respective air nozzles are not activated and the object falls down into a container for the non-metallic objects, when the objects reach the end of the conveyer belt.

In those metal sorting devices, the inventors discovered that the conveyer belt gets damaged over long-term usage, because of metallic dust, nails or scraps which get stuck in the belt over time. This damage may influence the sorting quality. For example, false detections could cause the air nozzles to blow on non-metallic objects, because the loose non-metallic object lays on a metallic contaminant which is stuck in the belt, which could lead to impurities in the sorting result.

A solution could be increasing a threshold value at which the air nozzles are activated for old conveyer belts. This way, small contaminants which are stuck in the conveyer belt, would not lead to an activation of the air nozzles. However, this would have the disadvantage that small metallic objects would not be detectable anymore.

SUMMARY OF THE INVENTION

The present invention provides a method and apparatus for analyzing objects depending on their electromagnetic properties, which may improve a detection quality.

According to an embodiment of the invention, a method for analyzing objects depending on their electromagnetic properties, such as for analyzing and sorting them into non-metallic and metallic objects, and/or such as for analyzing and sorting the metallic objects according to their kind of metal, is provided. The method comprising the steps of conveying the objects to be analyzed on a conveyer belt; scanning the electromagnetic properties of the objects and the conveyer belt by an electromagnetic sensor, wherein the electromagnetic properties of the conveyer belt are dependent on metallic contaminants which are stuck in the conveyer belt; generating belt properties data representing the electromagnetic properties of the conveyer belt (including its contaminants) only, and analyzing the objects according to the scanned electromagnetic properties and the belt properties data. The mentioned method steps are not listed in the order of their execution. Just as an example, the step of generating belt properties data can be executed prior to the conveying of the objects, in case the generating is realized by means of a calibration step. Also, the step of generating belt properties data can be executed while the objects are conveyed, in case the generating is realized by means of a learning process. Or the generation is realized by implementing both. In particular, the objects are sorted into metallic and non-metallic objects which can be determined by way of their electromagnetic properties. Additionally or alternatively, the objects could also be sorted according to the kind of metal they comprise or are made of. The contaminants being stuck in the conveyer belt means that they did not fall off the conveyer belt in a previous conveying cycle when reaching the turnaround point and did also not fall off when being moved upside down along the underside of the conveyer belt, such that these contaminants again enter the consecutive conveying cycle. This does not necessarily mean that it is not possible that these contaminants get loose later and fall off in a later conveying cycle. As a conveyer belt is by nature a flat strap-shaped structure, the surface area refers to the surface area which is provided for carrying the objects to be analyzed. This embodiment has the benefits that the electromagnetic properties of the conveyer belt, namely the influence of metallic contaminants which are stuck in the conveyer belt, are considered when analyzing the objects, e.g. when distinguishing between metallic and non-metallic objects which have to be analyzed. This way, the objects which are stuck in the conveyer belt influence the analysis less, which may improve sorting results in case the method is used for sorting.

Thus, the gist of the invention may lay in that the conveyer belt properties, in particular the electromagnetic properties of the conveyer belt due to metallic objects which are stuck in the conveyer belt, are considered in the analysis of the objects which lay loosely on the conveyer belt and which are conveyed by the conveyer belt. Up to now, to the knowledge of the inventors, these contaminants have not been considered in the analysis of the objects yet, and also the necessity to consider these contaminants has not been recognized. During the method according to the above embodiment of the present invention, the operation may have different stages. During an initial stage, a calibration may be conducted, in which only the belt is scanned without loose objects lying on the belt. This way, the belt properties data can be directly achieved without comparing the scan results with previous scan results. In a later stage, the conveyer belt is conveying loose objects to be analyzed. During this stage the belt properties data are adapted during every new conveying cycle. This means, the above step of generating belt properties data representing the electromagnetic properties of the conveyer belt, covers the generation of belt properties data by means of a calibration stage and it also covers the generation of belt properties data by means of adapting the belt properties data. However, the step of generating belt properties data does not necessarily have to comprise both, because an improvement over the state of the art can already be achieved by only conducting a calibration step without the later adaption step, and also by only conducting the adaptation step without the calibration step. When conducting the calibration step prior to the adaptation step, the correct belt properties data are available faster and right from the beginning. However, also without the calibration step, correct belt properties data can be achieved after a number of conveying cycles. In case a calibration and/or adaptation is used, the calibration is usually conducted once before starting the continuous operation and the adaptation step is conducted repeatedly during the normal operation, following a calibration (if there is one).

The step of scanning the electromagnetic properties of the objects and the conveyer belt by an electromagnetic sensor means that the electromagnetic properties of the objects are scanned simultaneously with the electromagnetic properties of the conveyer belt. As already mentioned above, during a possible calibration stage, there are no objects (no loose objects) present, but only the contaminants (objects which are stuck in the conveyer belt) therefore, during a calibration step, only the electromagnetic properties of the conveyer belt (which includes the contaminants) are scanned. The step of scanning the electromagnetic properties of the objects and the conveyer belt refers to the normal operation following the calibration stage, in which the objects lay on the conveyer belt and therefore, as a matter of course, only both can be scanned together, the electromagnetic properties of the conveyer belt and the electromagnetic properties of the objects.

According to a further embodiment of the invention, the method further comprises the step of saving the generated belt properties data in a data base, in particular a Random Access Memory (RAM).

According to a further embodiment of the invention, the step of analyzing is a step of classifying the objects. In particular, this is a classification into non-metals or metals, or a classification into non-metals and different metals, e.g. non-metals, copper, aluminum, iron, steel, gold, silver, etc., or the classification into different metals. This classification may be used for sorting the objects.

According to a yet further embodiment of the invention, the method sorts the objects according to their classification, into non-metals and metals, or into non-metals and different kind of metals, or into different kind of metals.

According to a further embodiment of the invention, in the method, the belt properties data are generated by a learning process in which the belt properties data are determined by comparing current scanned electromagnetic properties of the objects and the conveyer belt with scanned electromagnetic properties of the objects and the conveyer belt of one or more previous conveying cycles of the conveyer belt.

According to a further embodiment of the invention, in the method, the belt properties data are generated by adapting the belt properties data by comparing the electromagnetic properties detected at a specific spot of the electromagnetic sensor in a current conveying cycle at a specific cycle time with the electromagnetic properties of the same spot in a previous conveying cycle at the same cycle time. Adapting may include overwriting previous belt properties data with newly determined belt properties data. The same cycle time means the same time spot within a full conveying cycle, i.e. after the conveyer belt run for an entire loop. This way, the method for analyzing is able to constantly determine the electromagnetic properties of the conveyer belt, such as if there are metallic objects stuck in the belt and their position, and to adapt the analysis to the changing conveyer belt properties, because due to metallic objects getting stuck in the conveyer belt and getting loose again and or newly stuck metallic objects, the electromagnetic properties of the conveyer belt may change over time. Further, it is considered when such a damaged conveyer belt shifts in a direction perpendicular to the conveying direction and thus is shifted relative to the electromagnetic sensor.

According to a yet further embodiment of the invention, in the method, the adaptation of the belt properties data is dependent on the number of conveying cycles, out of a certain number of conveying cycles, in which the electromagnetic properties of the conveyer belt detected at the specific spot of the electromagnetic sensor at a specific conveying cycle time were detected to be metallic. In particular, persistently detected stuck objects gradually fade into the belt properties data or the sorting decision at a given learning rate, on the other hand, rarely detected stuck objects are erased from the belt properties data or the sorting decision over time. For example if it is detected that a metallic object just got stuck in the belt, it may be likely that it will get loose again in the next conveying cycle. Therefore, it is beneficial to consider the frequency of the presence of a certain stuck metallic object.

According to a further embodiment of the invention, the method further comprises the step of assigning a specific spot of the electromagnetic sensor at a specific conveying cycle time a specific classifier, in particular one or more threshold values, according to which a classification of the objects is made, wherein the classifier is determined from the belt properties data. In particular, the classifier is one or more threshold values. In case of classifying between non-metallic and metallic objects, one threshold value per specific spot is sufficient. In case of classifying different kinds of metal, more than one threshold values are necessary depending on the number of different metals that shall be classified. Also, instead of a threshold value, the classifier can also be a map. In practice, the sorting decision, namely if an object is forwarded into a container for metallic objects or a container for non-metallic objects may be made based on a signal indicating the electromagnetic properties at a certain spot where the object is located, if this detected signal is larger or smaller it is concluded that the object is metallic or non-metallic.

According to a further embodiment of the invention, in the method, the belt properties data are generated by calibrating in which the conveyer belt is run for at least one conveying cycle without conveying objects to be analyzed, and during which the electromagnetic properties of the conveyer belt are detected at plural spots of the electromagnetic sensor and for plural conveying cycle times. In particular, each spot is assigned a specific threshold value and assigned x and y coordinates with respect to the electromagnetic sensor. This calibration phase has the benefit that right from the beginning, there is conveyer properties data available which give a correct image of the conveyer belt and its contaminants, such that the sorting quality is already high from the beginning.

According to a yet further embodiment of the invention, the method further comprises the steps of monitoring the belt properties data, determining a contamination degree of the conveyer belt, and indicating the contamination degree to a user. The indication may be a visual or acoustic indication using a monitor, display, light, or sound generator. In this embodiment, the contamination degree of the conveyer belt may be indicated continuously or only when a certain contamination degree is reached, such as when the contamination with contaminants of the conveyor belt is above a certain threshold value or a certain percentage of contamination relative to a total conveying surface area. This embodiment has the benefit that the user is informed about the conveyer belt status and can take necessary actions, such as an exchange of the belt or cleaning of the belt, when an undesired level of contamination is reached.

According to a further embodiment of the invention, the method is adapted such that a contamination of the conveyer belt is graphically illustrated to a user by illustrating a graphical reproduction or image of a partial area of the conveyer belt and illustrating within this reproduction or image the contaminations as areas according to their size and location on the conveyor belt.

The following embodiments are directed to an apparatus. These embodiments have the same advantages, as mentioned in connection with the corresponding method embodiments. Comments on the meaning and interpretation of features and terms given above also apply to the corresponding apparatus features.

According to a yet further embodiment of the invention, an analyzing apparatus for analyzing objects depending on their electromagnetic properties is provided. The apparatus comprises a conveyer belt for conveying the objects to be analyzed; an electromagnetic sensor for scanning the electromagnetic properties of the objects and the conveyer belt, wherein the electromagnetic properties of the conveyer belt are dependent on metallic contaminants which are stuck in the conveyer belt; a calculation unit, such as a processor or a unit of the processor, for generating belt properties data representing the electromagnetic properties of the conveyer belt (including its contaminants) only, and an analyzing unit, such as a processor or a unit of the processor, for analyzing the objects according to the scanned electromagnetic properties and the belt properties data.

According to a further embodiment of the invention, the analyzing apparatus further comprising a memory for saving the generated belt properties data.

According to a further embodiment of the invention, the analyzing unit is adapted to classify the objects.

According to a further embodiment of the invention, the analyzing apparatus further comprises a sorting device for sorting the objects, according to their classification, into non-metals and metals, or into non-metals and different kind of metals, or into different kind of metals.

According to a further embodiment of the invention, the analyzing apparatus is designed such that the calculation unit is adapted to conduct a learning process in which the belt properties data are determined by comparing current scanned electromagnetic properties of the objects and the conveyer belt with scanned electromagnetic properties of the objects and the conveyer belt of one or more previous conveying cycles of the conveyer belt.

According to a further embodiment, the apparatus is designed such that the calculation unit is adapted to adapt the belt properties data by comparing the electromagnetic properties detected at a specific spot of the electromagnetic sensor in a current conveying cycle at a specific cycle time with the electromagnetic properties of the same spot in a previous conveying cycle at the same cycle time.

According to a further embodiment, the adaptation of the belt properties data is dependent on the number of conveying cycles, out of a certain number of conveying cycles, in which the electromagnetic properties of the conveyer belt detected at the specific spot of the electromagnetic sensor at a specific conveying cycle time were detected to be metallic.

According to a further embodiment, the calculation unit is adapted to assign a specific spot of the electromagnetic sensor at a specific cycle time a specific classifier according to which a classification of the objects is made, wherein the classifier is determined from the belt properties data.

According to a further embodiment, the electromagnetic sensor comprises a first array of electromagnetic metal sensor coils.

According to a further embodiment, the electromagnetic metal sensor coils of the first array are arranged along a sensor line extending substantially perpendicular to the conveying direction and substantially in parallel to the surface area of the conveyer belt.

According to a further embodiment, a second array of electromagnetic metal sensor coils is provided, which are arranged along a line which is parallel to the sensor line and arranged downstream in a conveying direction.

According to a further embodiment, the electromagnetic metal sensor coils of the first array are offset in a direction along the sensor line with respect to the electromagnetic metal sensor coils of the second array. This has the advantage of a better coverage of the area which is to be scanned.

According to a yet further embodiment, the apparatus further comprises nozzles as sorting device for blowing selected objects into a container or into a specific container out of more containers. Additionally or alternatively mechanical fingers could be provided as sorting device, which for example grab, move and drop the objects into the respective container. Blowing the selected objects is only one of several available means for sorting the objects after analyzing them.

According to a further embodiment of the invention, the apparatus further comprises a monitoring unit, such as a processor or a unit of the processor, for monitoring the belt properties data and for determining a contamination degree of the conveyer belt, and an indication device indicating the contamination degree to a user. The indication device may be a visual or acoustic indication device such as a monitor, display, light, or sound generator. In this embodiment, the contamination degree of the conveyer belt may be indicated continuously or only when a certain contamination degree is reached, such as when the contamination with contaminants of the conveyor belt is above a certain threshold value or a certain percentage of contamination relative to a total conveying surface area.

According to a further embodiment of the invention, the apparatus is further comprising an indication device for graphically illustrating to a user a contamination of the conveyer belt by illustrating a graphical reproduction or image of a partial area of the conveyer belt and illustrating within this reproduction or image the contaminations as areas according to their size and location on the conveyor belt.

These and other embodiments are described in the following in more detail with reference to the Figures.

BRIEF DESCRIPTION OF THE FIGURES

FIG. 3*a* visualizes the scanning result during operation, the visualization shows metallic objects to be analyzed and metallic objects stuck in the conveyer belt of the apparatus of FIG. 1;

FIG. 3*b* visualizes the belt properties data in form of a background image which shows where metallic objects are stuck in the conveyer belt of the apparatus of FIG. 1;

FIG. 3*c* visualizes a correction of FIG. 3*a*, in which FIG. 3*b* is used to correct FIG. 3*a*;

FIGS. 4*a* to 4*e* visualize the gradual adaption of the conveyer properties data after 0 conveying cycles (FIG. 4*a*), 10 conveying cycles (FIG. 4*b*), 20 conveying cycles (FIG. 4*c*), 35 conveying cycles (FIG. 4*d*), and 50 conveying cycles (FIG. 4*e*);

DETAILED DESCRIPTION OF EXEMPLARY EMBODIMENTS OF THE INVENTION

Figure 1:
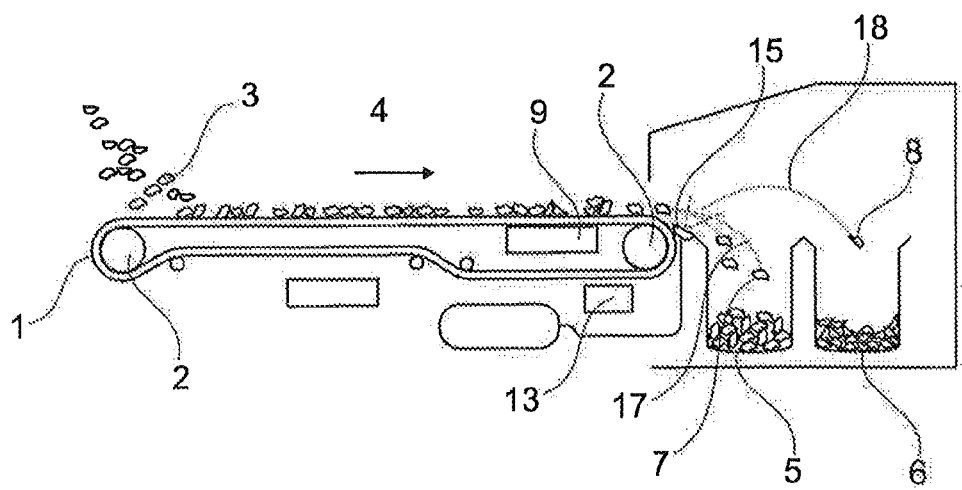
FIG. 1 schematically shows an apparatus according to an embodiment of the invention.
Figure 2:
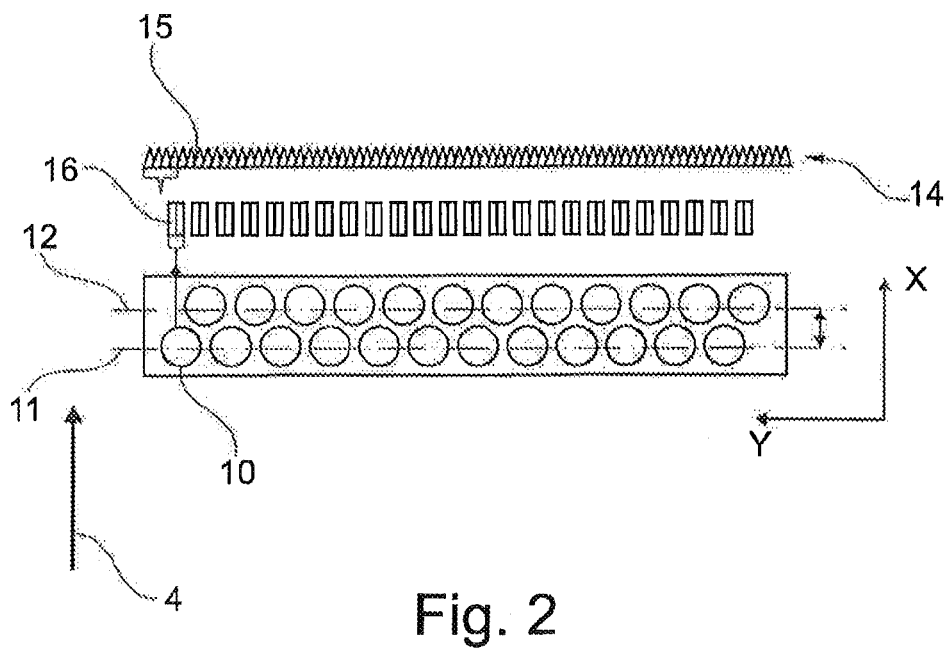
FIG. 2 schematically shows a section of the apparatus of FIG. 1.

FIG. 1 shows an apparatus for sorting objects, such as garbage or recyclable objects, according to an embodiment of the invention. In particular, the apparatus sorts out metallic objects from a stream of conveyed objects. Additionally or alternatively, the apparatus could also sort different kinds of metal, namely whether the object comprises or is made of copper, aluminum, iron, steel, gold, silver, etc. The apparatus comprises an endless loop conveyer belt 1 which is for example made of flexible non-magnetic material provided in form of one or more layers. The material is for example an elastomer. The conveyer belt 1 is driven by at least two pulleys 2 in a known manner, in order to move objects 3 to be analyzed (in particular objects to be sorted) along a conveying direction 4. While being moved above a later described electromagnetic sensor, the objects 3 are analyzed. At the turnaround point (with respect to the conveying direction) of the conveyer belt 1, two or more containers 5, 6 are provided. At this turnaround point of the conveyer belt 1, the objects 3 to be analyzed are divided (sorted) into non-metallic objects 7 and metallic objects 8. In this embodiment, the container 5 is intended for collecting the non-metallic objects 7, and the container 6 is intended for collecting the metallic objects 8.

In order to distinguish between metallic and non-metallic objects, an electromagnetic sensor 9 is provided which comprises a plurality of electromagnetic metal sensor coils 10, the working principle of which is known from the state of the art. For example U.S. Pat. No. 6,696,655 B2 describes sensor coils which could be used in connection with this invention. These electromagnetic metal sensor coils 10 are positioned near the conveyer belt 1. The sensor coils 10 are electrically excited and the presence of a metal object near such a sensor coil will lead to a certain characteristic electric signal output from the sensor coils 10 from which it can be determined whether the object is non-metallic or metallic and in which it may even determined which kind of metal it is (e.g. gold, silver, iron, aluminum, etc.). Also, other metal detectors known from the state of the art and can be used in the electromagnetic sensor 9.

Figure 6:
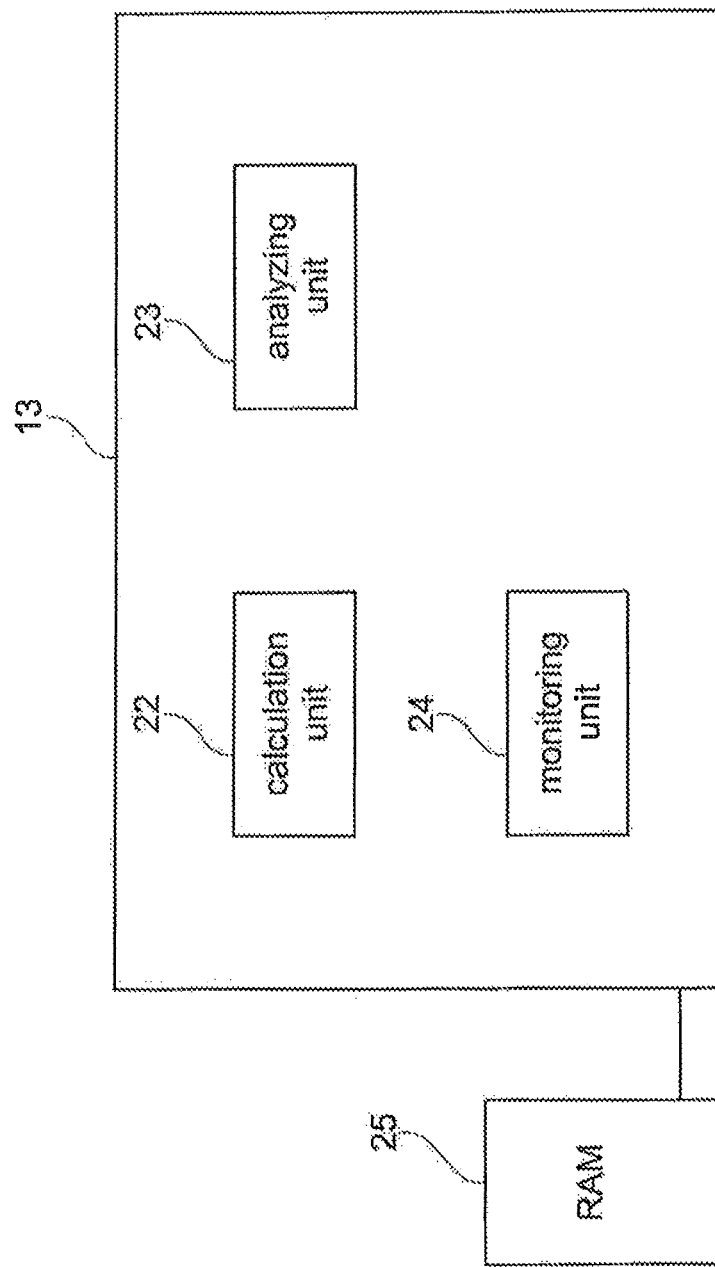
FIG. 6 illustrates a processor of the apparatus of FIG. 1 in more detail.

The plurality of electromagnetic metal sensor coils 10 comprises a first and second array of sensor coils 10, which are located underneath the conveyer belt 1 at a position at which the conveyer belt 1 carries objects 3 to be analyzed on its surface area. The sensor coils 10 of the first array are evenly distributed along a sensor line 11 extending substantially perpendicular, in particular perpendicular, to the conveying direction 4 and substantially in parallel, in particular in parallel, to the surface area of the conveyer belt 1. Further, a second array of sensor coils 10 is provided, wherein the sensor coils 10 of the second array are evenly distributed along a line 12 which is parallel to the sensor line 11 and arranged downstream in the conveying direction 4. The electromagnetic metal sensor coils 10 of the first array are offset in a direction along the sensor line 11 with respect to the electromagnetic metal sensor coils 10 of the second array, such that the distance, along the conveying direction 4, between the sensor line 11 and line 12 is smaller than a diameter of a sensor coil 10. Moreover, the sensor coils 10 may substantially extent over the entire breadth of the conveyer belt 1. According to the material of the object 3 which is passing by a specific sensor coil 10, an electric signal is output to a calculation unit 22 (see FIG. 6), such as a processor 13 (see FIGS. 1 and 6) or a unit of the processor 13. In this embodiment, by evaluating the signal, it can be determined whether the passing object 3 vertically above this specific electromagnetic metal sensor coil 10 is non-metallic or metallic. Additionally to this, or alternative to this, the signal can be used to determine what kind of metal the object 3 to be analyzed is comprising or made of, wherein for these modes more than the two shown containers 5, 6 may be provided. The processor 13 shown in FIG. 1, may comprise different units, as shown in FIG. 6, such as the calculation unit 22 for generating belt properties data representing the electromagnetic properties of the conveyer belt, an analyzing unit 23 for analyzing the objects according to the scanned electromagnetic properties and the belt properties data, and a monitoring unit 24 for monitoring the belt properties data and for determining a contamination degree of the conveyer belt. The splitting into different units includes for example the provision of different hardware units or chips, or the realizing of the mentioned functionality by means of programming executed by the same processor 13. The processor 13 is connected with a memory 25 such as a RAM for storing the belt properties data.

Downstream (in a conveying direction) of the electromagnetic sensor 9 and close to the turnaround point of the conveyer belt 1, where the objects 3 fall off the conveyer belt 1, there is provided an array 14 of jets or nozzles 15 which are evenly distributed along a line which is substantially parallel, in particular parallel, to the sensor line 10. The nozzles 15 may be positioned close to the trajectory 17 along which the non-metallic objects 7 fall off the conveyer belt 1 into the container 5. Each individual nozzle 15, or a smaller group of nozzles 15, can be controlled or activated via an associated valve 16.

In the case, in which according to the later described routine, it is determined that a loose metallic object 8 is present at a position vertically above this sensor coil 10, knowing the conveying speed and the distance between the specific sensor coil 10 and the respective downstream nozzle 15, the processor 13 determines the time when this detected metallic object 8 passes the respective nozzle 15 (which is located at the corresponding width position) and actives the respective valve 16 such that the metallic object 8 is air blown along a trajectory 18 into the container 6.

In case nothing or a non-metallic object 7 is present at a position vertically above this sensor coil 10, the respective downstream nozzle 15 is not activated and the non-metallic object 7 falls along the trajectory 17 into the container 5.

As described in the introductory part of this specification, the conveyer belt can get damaged over long-term usage, because of metallic objects, like dust, nails, scraps etc., which get stuck in the conveyer belt 1. This damage may influence the sorting quality. In order to counteract this, the apparatus learns the electromagnetic properties or the electromagnetic characteristic of the conveyer belt 1 during operation and adapts the control of the sorting such that the changing conveyer belt properties are considered when distinguishing between metallic and non-metallic objects.

Figure 5:
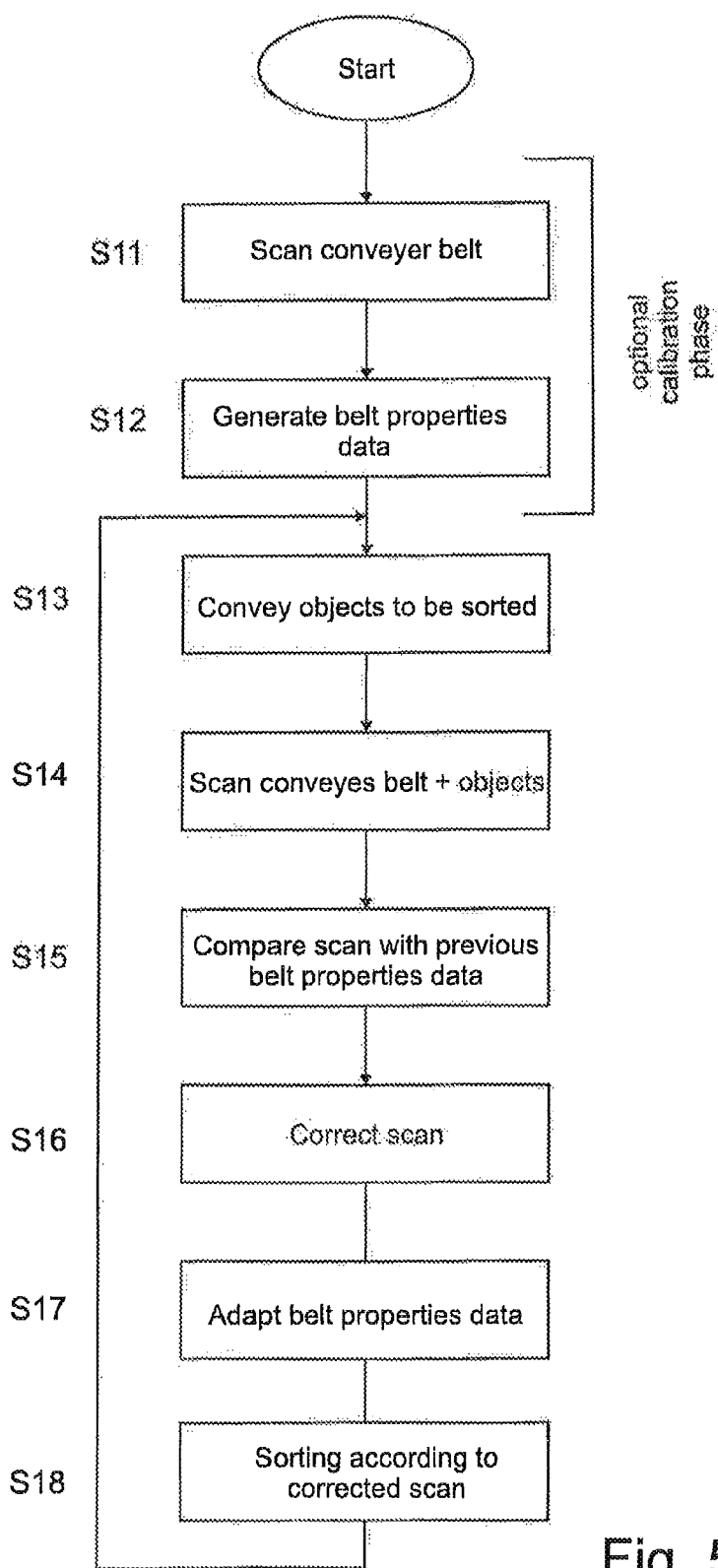
FIG. 5 illustrates a flow chart for executing the method for sorting according to an embodiment of the invention.

In order to do so, the apparatus may first conduct a calibration phase in which the conveyer belt 1 is run for at least one conveying cycle which is the movement over one loop. In this calibration phase, belt properties data representing the electromagnetic properties of the conveyer belt 1 along a surface area is generated. In more detail, the breadth of the electromagnetic sensor 9 is divided into a plurality of spots, in particular each of these spots corresponds to the detection scope vertically above one of the sensor coils 10 in case the electromagnetic sensor 9 is constructed like described above, according to the breadth (perpendicular to conveying direction 4) position, each of these spots has a certain y coordinate in a coordinate system which is fixed relative to the electromagnetic sensor 9 and shown in FIGS. 2 and 3*a*-3*c*. The length of the conveyer belt 1, which defines one conveying cycle (which is a full loop of the conveyer belt) is also divided up into a plurality of conveying cycle times, each time has a certain x coordinate in the above mentioned coordinate system. This way, the entire surface area of the conveyer belt 1 is identifiable with a certain x and y position, but this x and y position, or at least the y position is fixed relative to the electromagnetic sensor 9, because over time, the conveyer belt might shift in a direction perpendicular to the conveying direction and relative to the electromagnetic sensor 9. For each of these spots, the electromagnetic properties of the conveyer belt 1 are determined by means of the sensor coils 10 and saved, see step S11 in FIG. 5. Having these belt properties data, the processor 13 can determine, if the conveyer belt comprises metallic contaminants and where these contaminants are located, and generate belt properties data, see S12 in FIG. 5. The processor 13 can assign each of these spots via their x and y positions a threshold value which indicates the distinguishing limit between metallic or non-metallic objects.

It is to be noted that the calibration phase is optional and the belt properties data can also be determined via the later described adaptation (learning process). The benefit of the calibration phase is that it provides the correct conveyer properties right from the beginning of operation which can shorten the learning process.

The belt properties data can be in the form of a data file, which defines the electromagnetic characteristic over the entire surface area of the conveyer belt relative to the x-y-coordinate system described above. FIGS. 3*a* to 4*e* visualize such data files in form of images.

Figures 3A, 3B, 3C:
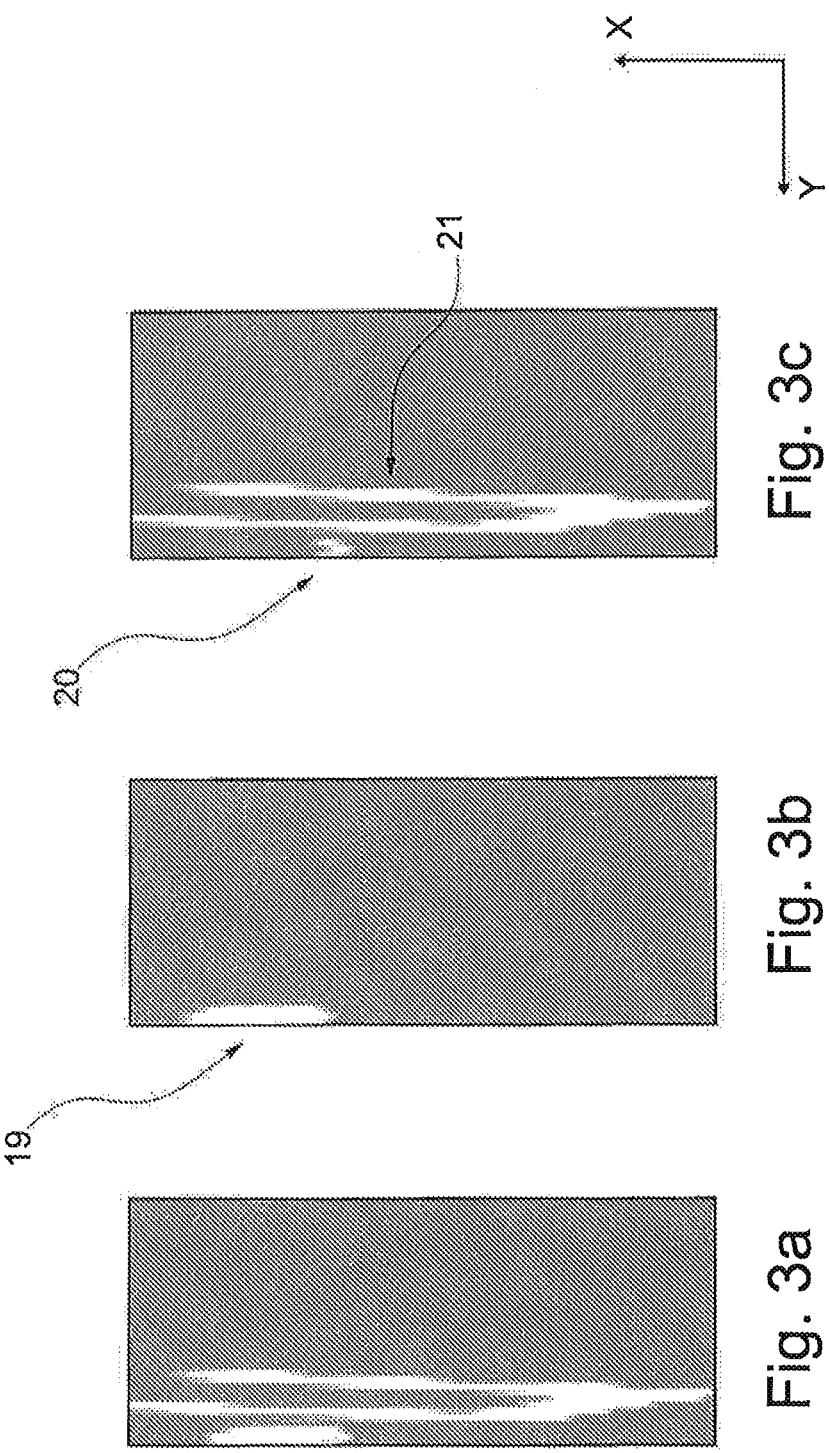

FIGS. 3*a* to 3*c* visualize the functionality of the apparatus in more detail. When the operation of the apparatus is started, the above described calibration phase is conducted which delivers initial belt properties data, see S12 in FIG. 5. These initial belt properties data can be visualized like in FIG. 3*b*. In FIG. 3*b*, the presence of metal is visualized white and the absence of metal is visualized black. As the conveyer belt 1 carries no loose object to be analyzed during the calibration phase, the white spot in FIG. 3*b* can easily identified as metallic object which is stuck in the conveyer belt 1. Or in visual terms, the processor learnt a background conveyer belt image which is shown in FIG. 3*b*.

When the objects 3 to be analyzed are conveyed on the conveyer belt 1 (see S13 in FIG. 5), the conveyer belt 1, including its metallic contaminants 19, and the objects 3 which are lying loosely on the conveyer belt 1 are scanned by means of the sensor coils 10 as described above, see S14 in FIG. 5. During this scanning electromagnetic data are obtained line-wise (lines along the y-direction) while the conveyer belt 1, including its metallic contaminants 19, and the carried loose objects 3 is passing by the electromagnetic sensor 9. From these electromagnetic data each spot scan can be determined as being metallic or non-metallic, as visualized in FIG. 3*a*. The data gathered from the current scan are handled similarly to the above described belt properties data. The current scan is in particular handled as a data file for which the breadth of the electromagnetic sensor 9 is divided into a plurality of spots, in particular each of these spots corresponds to the detection scope vertically above one of the sensor coils 10 in case the electromagnetic sensor 9 is constructed like described above, according to the breadth position, each of these spots has a certain y coordinate in a coordinate system which is fixed relative to the electromagnetic sensor 9 and shown in FIGS. 2 and 3*a*-3*c*. The length of the conveyer belt 1, which defines one conveying cycle is also divided up into a plurality of conveying cycle times, each of these times has a certain x coordinate in the mentioned coordinate system. This current electromagnetic data (visualized in FIG. 3*a*) would indicate that metallic objects are present at the white areas. However, from the calibration phase, or a previous conveying cycle, the processor knows via the belt properties data that the contaminant 19 was already there and is a metal object stuck in the belt. Therefore, this metallic object 19 is not considered as a loose metallic object 6 which has to be blown into the container 6, and is deleted in a corrected data set, as shown by reference number 20. In order to do so, the current electromagnetic data is compared with previous belt properties data, see S15 in FIG. 5, or in more detail the current electromagnetic data is corrected, see S16 in FIG. 5, by subtracting the previous belt properties data (which can either come from a calibration phase or a previous conveying cycle). Or in other words, the background image visualized in FIG. 3*b* is subtracted from the current input image shown in FIG. 3*a* such that FIG. 3*c* results which does only show the loose metallic objects 21 as metallic objects which can be blown into the container 6, see S18 in FIG. 5. This may be practically realized by increasing the threshold for activating the nozzles 15 for spots where the metal contaminants 19 are located such that even if the contaminant 19 is present, the spot is not considered as metallic when controlling the nozzles 15, unless an additional loose metallic object 8 is placed at this spot during the further operation. This way, the threshold which defines the limit for distinguishing between the presence or absence of metal (or between different kinds of metal) is continuously adapted during the operation of the apparatus and saved based on x and y position.

Over time, new contaminants 19 might get stuck in the conveyer belt, or present contaminants 19 might get loose. In order to adapt the belt properties data (background image $BG_t$) to this, see S17 in FIG. 5, the belt properties data (background image $BG_t$) is updated with respect to the difference $\Delta$ to the current electromagnetic data (current image $\text{Image}_t$) according to the following formula:

$$BG_t = (1-\Delta \cdot \alpha) \cdot BG_{t-1} + \alpha \cdot \Delta \cdot \text{Image}_t$$

In visual terms and in case the belt properties data is visualized as an image, this means that persistent metallic objects gradually fade into the background image at a given rate $\alpha$, whereas rare occurrences are gradually erased from the belt image over time.

In more abstract terms, the processor 13 determines the difference between the previous belt properties data and the current electromagnetic data gathered from the electromagnetic sensor 9. Then it updates the belt properties data gradually at a given learning rate $\alpha$. This way, if at a very same spot a new metallic object is present for several times, it gradually fades into the belt properties data as a newly stuck metallic contaminant 19. The learning rate requires that a metallic object has to be detected several times at the same spot in order to be identified as a new metallic contaminant 19. This way a metallic object which is just present during a single conveying cycle is not accidentally regarded as a contaminant 19. In other words, due to the learning rate, the presence of a new metallic contaminant 19 may increase a value indicative of the electromagnetic characteristic at this spot from 0 (for non-metallic) by the increment 1 in each conveying cycle. When 10 is reached, the spot is considered as being metallic and the associated threshold is increased accordingly.

FIGS. 4a to 4e visualize the gradual adaption of the conveyer properties after 0 conveying cycles (FIG. 4a), 10 conveying cycles (FIG. 4b), 20 conveying cycles (FIG. 4c), 35 conveying cycles (FIG. 4d), and 50 conveying cycles (FIG. 4e).

As already mentioned, the apparatus for sorting objects may comprise a monitoring unit 24, as a unit of the processor 13, for monitoring the belt properties data and for determining a contamination degree of the conveyer belt, and an indication device 26 indicating the contamination degree to a user.

Figure 7:
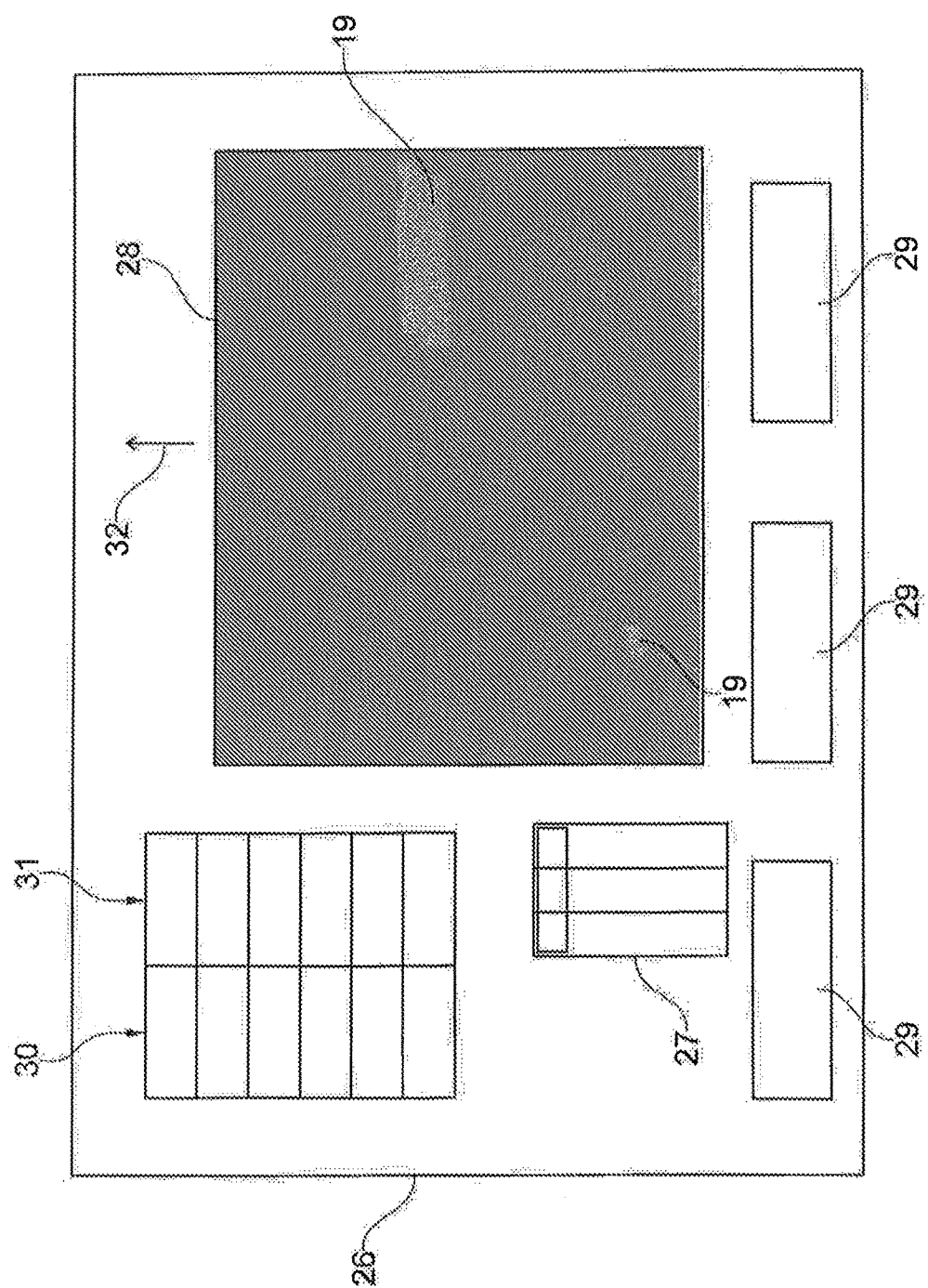
FIG. 7 illustrates an indication device for indicating the contamination degree to a user.

FIG. 7 illustrates the indication device 26 for indicating, amongst other information and parameter, the contamination of the conveyer belt 1 to the user. In particular, the indication device 26 is a screen of a monitor in which for example an overview 27 could be displayed. The overview 27 is illustrating a graphical reproduction of the entire conveyer belt 1 with its contaminants 19. Within this overview 27 a smaller frame could indicate which zoomed section of the conveyer belt 1 is illustrated in a detail window 28 showing a section of the conveyer belt 1 together with its contaminants 19 in more detail. In connection with the indication device 26, both, the illustrated conveyor belt 1 and the contaminants 19 are graphical reproductions of the same, however, it could also be a live stream showing the camera image output. Further, the indication device 26 could comprise some buttons 29 which could be real buttons or graphically illustrated buttons to be clicked on by means of a pointer device (e.g. a computer mouse), or they could be input boxes for entering control values for controlling the apparatus and method. Moreover, the indication device 26 could have a plurality of display fields in which for example parameters of the analyzing method and/or the analyzing apparatus are shown as indicated by reference numeral 30, and fields in which the associated values to these parameters are illustrated as indicated by reference numeral 31. One such parameter could be a contamination degree, e.g. displayed as a percentage value. An arrow 32 could indicate the conveying direction to the user. As immediately apparent to the skilled person, the above description of the indication device 26 can only be a rough exemplary scheme. In practical realization there are numerous ways of illustrating the contamination and/or contamination degree to a user. Generally speaking, the indication device may be a visual or acoustic indication device connected to the processor 13, such as a monitor, display, light, or tone generator. In this embodiment, the contamination degree of the conveyer belt may be indicated continuously or only when a certain contamination degree is reached, such as when the contamination with contaminants of the conveyor belt is above a certain threshold value or a certain percentage of contamination relative to a total conveying surface area.

While in the described embodiment, the objects are analyzed in order to be sorted, the analysis could also be used for a different purpose, such as a classification in order to treat specific objects different, for example in order paint differently classified objects differently.

While in the described embodiment, the electromagnetic properties of the objects are scanned by means of conveying (moving) the objects and passing them by the electromagnetic sensor, it is of course also within the scope of the invention to scan the electromagnetic properties by moving the electromagnetic sensor passed the objects to be analyzed (along the conveying direction) and temporarily stopping the conveyer belt, or by moving the electromagnetic sensor passed the objects to be analyzed additionally to the conveying movement of the conveyer belt.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously.

The invention claimed is:

1. A method for analyzing objects depending on their electromagnetic properties, the method comprising:
   conveying objects to be analyzed on a conveyer belt;
   scanning electromagnetic properties of the objects and the conveyer belt by an electromagnetic sensor;
   generating belt properties data representing the electromagnetic properties of the conveyer belt, said belt properties data comprising information regarding the electromagnetic properties of the conveyer belt that are dependent on metallic contaminants which are stuck in the conveyer belt;
   determining a difference between previously generated electromagnetic properties of the belt and current electromagnetic properties of the belt;
   analyzing the objects according to the scanned electromagnetic properties and the belt properties data; and
   identifying a metallic contaminant as stuck in the conveyer belt only after it has been detected more than one time at a same position on the conveyer belt, and updating the belt properties data with said metallic contaminant identified as stuck in the conveyor belt.

2. The method according to claim 1, further comprising the step of saving the generated belt properties data in a data base.

3. The method according to claim 1, wherein the step of analyzing is a step of classifying the objects.

4. The method according to claim 3, wherein the objects, according to their classification, are sorted into non-metals and metals, or are sorted into non-metals and different kind of metals, or are sorted into different kind of metals.

5. The method according to claim 1, wherein the belt properties data are generated by a learning process in which the belt properties data are determined by comparing current scanned electromagnetic properties with scanned electromagnetic properties of one or more previous conveying cycles of the conveyer belt.

6. The method according to claim 1, wherein the belt properties data are generated by adapting the belt properties data by comparing the electromagnetic properties detected at a specific spot of the electromagnetic sensor in a current conveying cycle at a specific cycle time with the electromagnetic properties of the same spot in a previous conveying cycle at the same cycle time.

7. The method according to claim 6, wherein the adaptation of the belt properties data is dependent on the number of conveying cycles, out of a certain number of conveying cycles, in which the electromagnetic properties of the conveyer belt detected at the specific spot of the electromagnetic sensor at a specific conveying cycle time were detected to be metallic.

8. The method according to claim 3, further comprising the step:
   assigning a specific spot of the electromagnetic sensor at a specific conveying cycle time a specific classifier according to which a classification of the objects is made, wherein the classifier is determined from the belt properties data.

9. The method according to claim 1, wherein the belt properties data are generated by calibrating in which the conveyer belt is run for at least one conveying cycle without conveying objects to be analyzed, and during which the electromagnetic properties of the conveyer belt are detected at plural spots of the electromagnetic sensor and for plural conveying cycle times.

10. The method according to claim 1, further comprising the steps:
monitoring the belt properties data, determining a contamination degree of the conveyer belt, and indicating the contamination degree to a user.

11. An analyzing apparatus for analyzing objects depending on their electromagnetic properties, comprising:
a conveyer belt for conveying the objects to be analyzed;
an electromagnetic sensor for scanning the electromagnetic properties of the objects and the conveyer belt;
a calculation unit for generating belt properties data representing the electromagnetic properties of the conveyer belt, said belt properties data comprising information regarding the electromagnetic properties of the conveyer belt that are dependent on metallic contaminants which are stuck in the conveyer belt;
a processor for determining a difference between previously calculated electromagnetic properties of the belt and current electromagnetic properties of the belt; and
an analyzing unit for analyzing the objects according to the scanned electromagnetic properties and the belt properties data,
the processor configured to identify a metallic contaminant as stuck in the conveyer belt only after it has been detected more than one time at a same position on the conveyor belt, and update the belt properties data with said metallic contaminant identified as stuck in the conveyor belt.

12. The analyzing apparatus according to claim 11, further comprising a memory for saving the generated belt properties data.

13. The analyzing apparatus according to claim 11, wherein the analyzing unit is adapted to classify the objects.

14. The analyzing apparatus according to claim 13, further comprising a sorting device for sorting the objects, according to their classification, into non-metals and metals, or into non-metals and different kind of metals, or into different kind of metals.

15. The analyzing apparatus according to claim 11, wherein the calculation unit is adapted to conduct a learning process in which the belt properties data are determined by comparing current scanned electromagnetic properties with scanned electromagnetic properties of one or more previous conveying cycles of the conveyer belt.

16. The analyzing apparatus according to claim 11, wherein the calculation unit is adapted to adapt the belt properties data by comparing the electromagnetic properties detected at a specific spot of the electromagnetic sensor in a current conveying cycle at a specific cycle time with the electromagnetic properties of the same spot in a previous conveying cycle at the same cycle time.

17. The analyzing apparatus according to claim 16, wherein the adaptation of the belt properties data is dependent on the number of conveying cycles, out of a certain number of conveying cycles, in which the electromagnetic properties of the conveyer belt detected at the specific spot of the electromagnetic sensor at a specific conveying cycle time were detected to be metallic.

18. The analyzing apparatus according to claim 11, wherein the calculation unit is adapted to assign a specific spot of the electromagnetic sensor at a specific cycle time a specific classifier according to which a classification of the objects is made, wherein the classifier is determined from the belt properties data.

19. The analyzing apparatus according to claim 11, wherein the electromagnetic sensor comprises a first array of electromagnetic metal sensor coils.

20. The analyzing apparatus according to claim 19, wherein the electromagnetic metal sensor coils of the first array are arranged along a sensor line extending substantially perpendicular to the conveying direction and substantially in parallel to the surface area of the conveyer belt.

21. The analyzing apparatus according to claim 20, wherein a second array of electromagnetic metal sensor coils is provided, which are arranged along a line which is parallel to the sensor line and arranged downstream in a conveying direction.

22. The analyzing apparatus according to claim 21, wherein the electromagnetic metal sensor coils of the first array are offset in a direction along the sensor line with respect to the electromagnetic metal sensor coils of the second array.

23. The analyzing apparatus according to claim 11, further comprising nozzles as sorting device for blowing selected objects into one or more containers.

24. The analyzing apparatus according to claim 11, comprising a monitoring unit for monitoring the belt properties data and for determining a contamination degree of the conveyer belt, and an indication device indicating the contamination degree to a user.

25. A method for analyzing objects depending on their electromagnetic properties, the method comprising:
conveying objects to be analyzed on a conveyer belt;
scanning electromagnetic properties of the objects and the conveyer belt by an electromagnetic sensor, the electromagnetic properties of the conveyer belt being dependent on metallic contaminants which are stuck in the conveyer belt;
generating belt properties data representing the electromagnetic properties of the conveyer belt,
updating the belt properties data gradually, whereby a newly stuck metallic contaminant is gradually introduced into the belt properties data so that is fully introduced in the belt properties data only after it has been detected several times at a same position on the conveyor belt, and
analyzing the objects according to the scanned electromagnetic properties and the updated belt properties data.

26. The method according to claim 25, wherein said newly stuck metallic contaminant is gradually introduced into the belt properties data in accordance with a given learning rate.

27. The method according to claim 26, wherein previously stuck metallic contaminants that have become loose are only gradually erased from the belt properties data so that they is fully removed from the belt properties data only after it has not been detected several times at a same position on the conveyor belt.

* * * * *